United States Patent [19]

Wetter et al.

[11] Patent Number: 5,190,555
[45] Date of Patent: Mar. 2, 1993

[54] DEVICE FOR COLLECTION AND REMOVAL OF BODY PARTS DURING LAPAROSCOPIC SURGERY

[75] Inventors: Lowell A. Wetter, San Francisco; Jeffrey E. Holmes, San Jose; Michael Hogendijk, Sunnyvale; Jeffrey J. Christian, San Jose, all of Calif.

[73] Assignee: Unisurge, Inc., Cupertino, Calif.

[21] Appl. No.: 807,098

[22] Filed: Dec. 13, 1991

[51] Int. Cl.⁵ ............................................. A61B 17/00
[52] U.S. Cl. ........................................ 606/114; 606/1; 606/113; 606/127
[58] Field of Search .............. 604/264, 171; 606/1, 606/108, 110, 113, 114, 127, 128

[56] References Cited

U.S. PATENT DOCUMENTS

| 30,471 | 10/1860 | Dudley | 606/127 |
|---|---|---|---|
| 156,477 | 11/1874 | Bradford | 606/127 |
| 3,908,661 | 9/1975 | Kramer | 606/127 |
| 4,557,255 | 12/1985 | Goodman | 606/127 |
| 5,074,867 | 12/1991 | Wilk | 606/128 |
| 5,084,054 | 1/1992 | Bencini et al. | 606/127 |

FOREIGN PATENT DOCUMENTS 0025796  1/1884  Brazil .................. 606/127

Primary Examiner—Stephen C. Pellegrino
Assistant Examiner—Glenn K. Dawson
Attorney, Agent, or Firm—Flehr, Hohbach, Test, Albritton & Herbert

[57] ABSTRACT

A device for the collection and removal of body tissue and/or parts in laparoscopic surgery having an elongated tubular member with proximal and distal extremities and a bore extending therethrough. A sack formed of a flexible material with an opening therein is secured by a rod inside the tubular member to the distal extremity of the elongated tubular member. A drawstring is secured to the sack and circumscribes the opening of the sack and controls the opening and closing of the sack. The drawstring extends into the bore and is connected to a slide mounted around the tubular member. A handle is secured to the proximal extremity of the tubular member and finger rings are secured to the proximal extremity of the slide. Movement of the slide towards the distal extremity of the tubular member opens the sack once inside the patient for receiving the tissue or body part, while movement of the slide in a distal direction causes the sack to close to capture the tissue or body part.

8 Claims, 2 Drawing Sheets

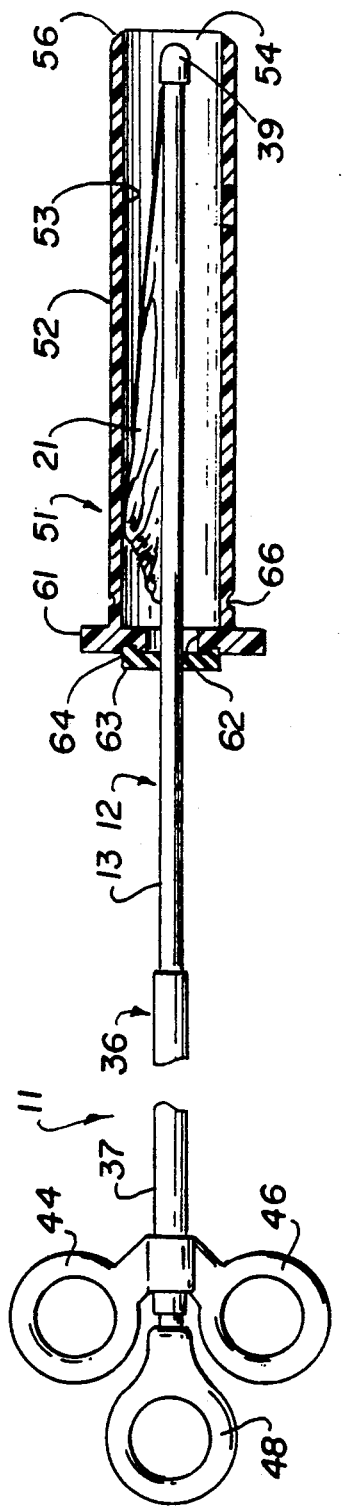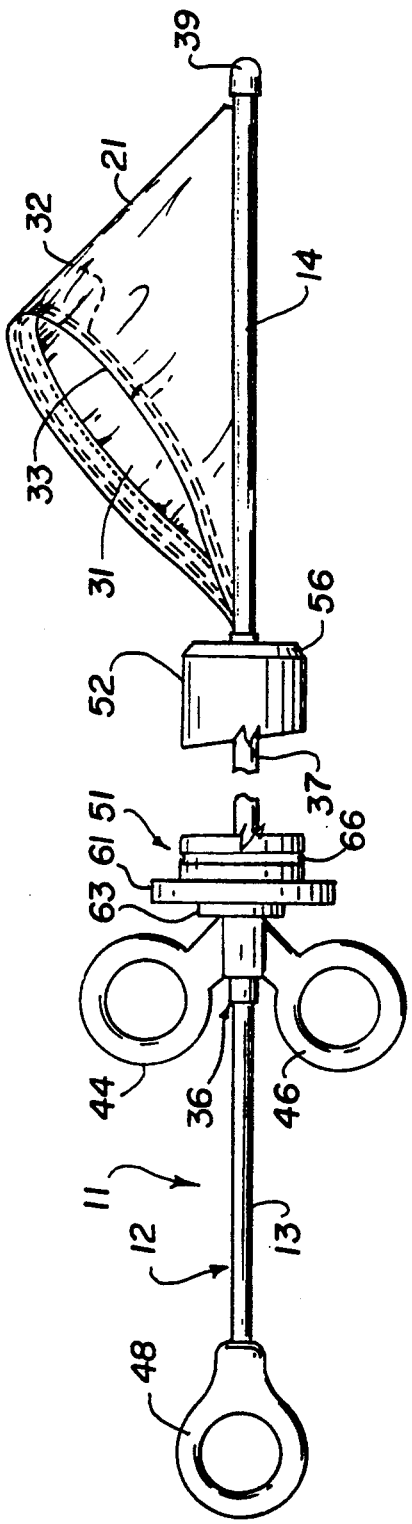

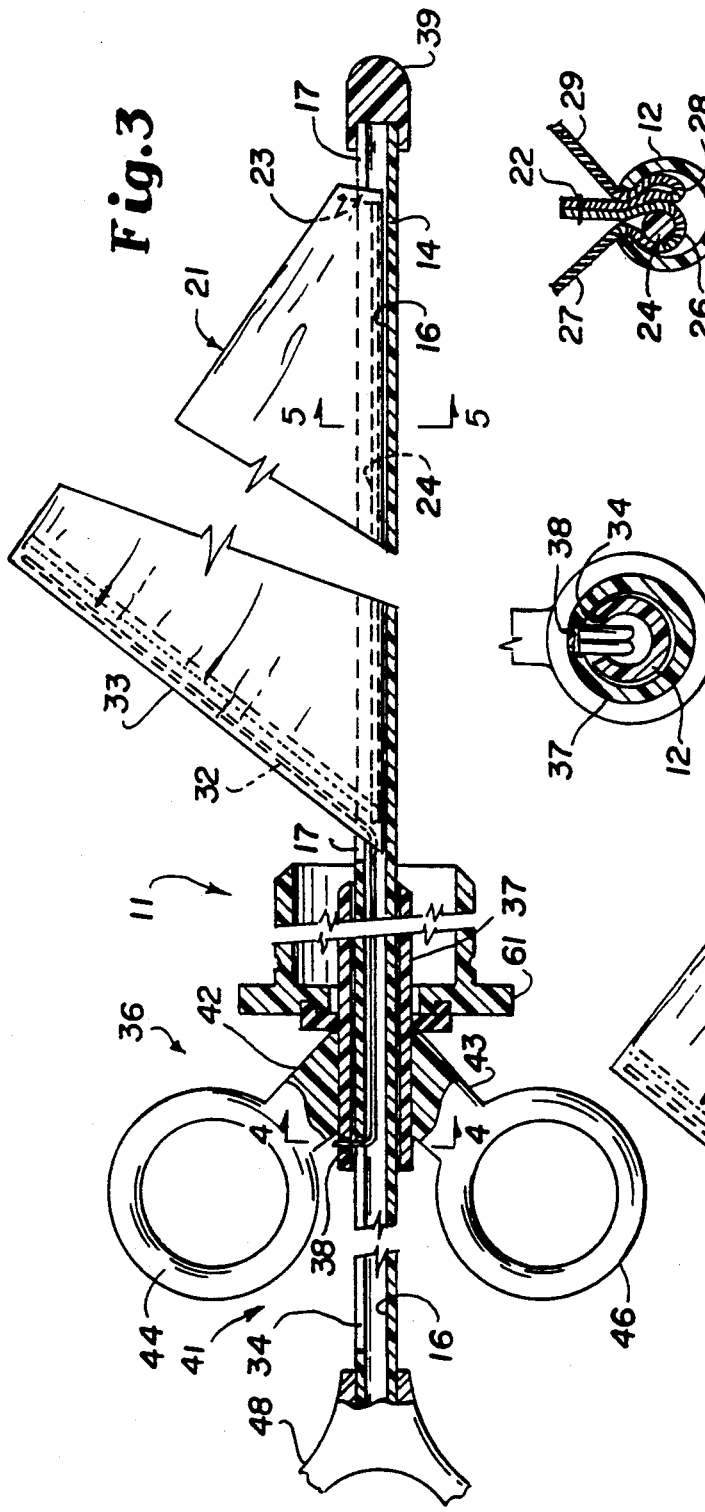

DEVICE FOR COLLECTION AND REMOVAL OF BODY PARTS DURING LAPAROSCOPIC SURGERY

This invention relates to a device for collection and removal of body parts and particularly to such a device suitable for use in endoscopic surgery.

In many laparoscopic procedures, there is a need to remove certain tissue as for example a diseased gallbladder. In the past, the removal of such tissue through the entry port in the abdominal wall placed a strain on the gallbladder causing it to burst and spilling its contents within the abdominal cavity which can lead to infection. There is therefore a need for a device which can facilitate the collection and removal of such tissue.

In general it is an object of the present invention to provide a device which facilitates the collection and removal of body tissue and in particular body parts.

Another object of the invention is to provide a device of the above character which is particularly useful in endoscopic surgery.

Another object of the invention is to provide a device of the above character in which the tissue or body part can be collected in an open-ended sack which after the collection can be closed during removal of the body part from the patient.

Another object of the invention is to provide a device of the above character in which the sack can be readily opened and closed.

Another object of the invention is to provide a device which can be readily inserted into the body cavity of the patient.

Another object of the invention is to provide a device of the above character which can be operated by one hand.

Additional objects and features of the invention will appear from the following description in which the preferred embodiments are set forth in detail in conjunction with the accompanying drawings.

FIG. 1 is a side elevational view of a device for the collection and removal of body parts incorporating the present invention with certain parts being shown in cross-section with the sack being in a closed position and retained in a tubular capsule.

FIG. 2 is a side elevational view of the device shown in FIG. 1 but showing the sack in an open position.

FIG. 3 is a side elevational view of the device shown in FIG. 2 shown with certain portions of the same being shown in cross-section.

FIG. 4 is a cross-sectional view taken along the line 4—4 of FIG. 3.

FIG. 5 is a cross-sectional view taken along the line 5—5 of FIG. 3.

FIG. 6 is a side elevational view partially in cross-section of another embodiment of a device incorporating the present invention.

FIG. 7 is a cross-sectional view taken along the line 7—7 of FIG. 6.

In general, the device for collection and removal of body tissue and/or parts in laparoscopic surgery from a patient is comprised of an elongate tubular member having proximal and distal extremities and having a passage therein. A sack formed of a flexible material is provided and has an opening therein. Means is carried by the tubular member for securing at least a portion of the sack to the distal extremity of the elongate tubular member. Drawstring means circumscribes the opening in the sack and is used for closing and opening said opening in said sack and extends into said elongate tubular member. Slide means is slidably mounted on said tubular member and is secured to said drawstring means in said tubular member for causing opening and closing of said opening in said sack as said slide means is moved longitudinally of the elongate tubular member. Handle means is secured to the proximal extremity of the tubular member and to said side means for introducing said sack into the body of a patient and for causing opening of said opening in the sack for the collection of body tissue from the patient and for closing the opening in the sack after collection of the tissue from the patient for removal of the same.

More particularly as shown in FIGS. 1 through 5 of the drawings, the device 11 for the collection and removal of body tissue and/or parts in laparoscopic surgery performed on a patient consists of an elongate tubular member 12 formed of a suitable relatively rigid plastic such as polycarbonate. The tubular member 12 can have a suitable outside diameter as for example ⅛ to ¼ inches and preferably a diameter of 0.150 inches with a wall thickness ranging from 0.015 to 0.30 inches and preferably a wall thickness of approximately 0.025. The tubular member 12 serves as a relatively rigid support shaft and is provided with a proximal extremity 13 and a distal extremity 14. It is provided with a central bore 16 extending the length thereof. A longitudinally extending slit 17 is provided in the distal extremity 14 and extends through the distal extremity 14 of the tubular member 12.

The device also includes a sack 21 formed of a suitable material such as a rip-stock fabric. The sack 21 is generally of a funnel-shape configuration and is formed from a piece of fabric that is folded onto itself. The edges are sewn together at a long seam 22 (see FIG. 5) extending along the length of the folded fabric and a short seam 24 extending along the distal extremity of the sack. The portion of the sack 21 having the seam 22 therein is slipped into the bore 16 and into the slit 17 so that one side of the sack 21 is retained within the bore 16. In order to ensure that the portion of the fabric at the seam is retained within the tubular member 12, a retaining rod 24 is positioned within a fold 26 provided in the side wall 27 of the sack 21. Similarly, a fold 28 is provided in the side wall 29 of the sack.

The sack 21 is provided with an open end 31 (see FIG. 2) and has a drawstring 32 slidably positioned within a hem 33 provided in the fabric at the open end. The drawstring 32 extends downwardly into the slit 17 and into the bore 16 toward the proximal extremity 13 of the tubular member 12 (see FIG. 3). The ends of the drawstring 32 extend upwardly out of the bore 16 through a longitudinally extending slot 34 provided in the proximal extremity 13 of the tubular member 12.

Slide means 36 is provided for retaining the ends of the drawstring 32 for moving the drawstring to open and close the open end 31 of the sack 21. This slide means consists of a co-axially mounted sleeve 37 formed of a suitable material such as plastic slidably mounted on the tubular member 12. The sleeve 37 can be also formed of the same plastic material as the tubular member 12 but has a relatively short length in comparison to the length of the tubular member 12. As can be seen from FIG. 3, the ends of the drawstring 32 are secured to the sleeve 37 at 38 as shown in FIG. 3 by suitable means such as an adhesive. A rounded atraumatic tip 39 is secured to the distal extremity of the tubular member 12 by suitable means such as an adhesive (not shown) and closes the slit 17 to provide additional means to prevent accidental removal of the sack 21 longitudinally of the slit 17.

Handle means 41 is provided for causing relative movement between the sleeve 37 and the tubular member 12 and consists of first and second diagonally extending arms 43 secured to the sleeve 37 by a suitable means such as an adhesive (not shown). First and second finger rings 44 and 46 are formed integral with the arms 42 and 43 and are adapted to be grasped by two fingers of a hand. Another finger ring 48 forms a part of the handle means 41 and is secured to the proximal extremity of the tubular member 12. By grasping the finger ring 48 and placing it in the palm of the hand and by having two other fingers of the same hand grasping the finger rings 44 and 46, the slide means 36 including the sleeve 37 can be pulled toward the finger ring 48 to pull the drawstring 32 to close the open end 31 and to collapse the sack 21 so that it is relatively compact and in a close proximity to the distal extremity of the tubular member 12.

In order to facilitate the introduction of the device 11 into a sheath typically used in laparoscopic surgery, the distal extremity 14 of the tubular member 12 with the sack in a collapsed position thereon is enclosed within a tubular capsule 51 (see FIG. 1). The capsule 51 consists of an introducer tube 52 formed of a suitable material such as plastic which is provided with a cylindrical cavity 53 therein which is of a size to accommodate the tubular member 12 with the collapsed sack 21 thereon. The cylindrical cavity 53 opens through an opening 54 in the distal extremity of the tube 52. The distal extremity of the tube 52 is provided with a taper 56. A cap 61 is provided on the other end of the tubular member 52 and is formed integral therewith. The cap 61 is provided with a bore 62 through which the tubular member 12 extends. Means is provided for forming a liquid-tight seal between the tubular member 12 and the cap 61 and consists of a seal 63 formed of a suitable elastomeric material which is seated in an annular recess 64 in the cap 61. An annular recess 66 is formed in the exterior surface of the tube 52 and is adapted to receive the O-ring like protrusion in the valve means as described in co-pending application, Ser. No. 07/757,343, filed Aug. 10, 1991, to hold the tubular member 52 in a desired position.

Operation and use of the device for the collection and removal of body tissue and/or parts in a laparoscopic procedure may now be described as follows. Let it be assumed that laparoscopic surgery is taking place and that a sheath has been placed in the abdominal cavity of the patient and that it is desired to remove body tissue or a body part which has been excised within the abdominal cavity. The device 11 with the capsule 51 thereon as shown in FIG. 1 is introduced into the sheath and into the body cavity with the tube 52 being seated within the sheath. The sack 21 is deployed by pushing it out of the capsule 52 by use of the handle means 41 through the opening 54 until it is clear of the tube 52. Thereafter, the fingers of the hand are utilized to grasp the finger rings 44 and 46 and to push them downwardly away from the finger ring 48 in the palm of the hand of the physician to cause the pull strings to be pushed downwardly of the bore 16 and to open the opening 31 in the sack 21. The Nylon TM monofilament line utilized for the drawstring has sufficient rigidity so that it causes the open end of the sack to bow outwardly into the oval shape shown in FIG. 2. After the sack 21 has been opened, it can be positioned in the desired location by the physician grasping the finger ring 48 with the positioning being observed in the laparoscopic procedure within the abdomen of the patient. For example, let it be assumed that it is desired to collect a diseased gallbladder which is being excised and placed into the sack 21.

The sack 21 can be readily positioned by the physician to receive the gallbladder as it is being excised and placed into the sack 21. As soon as it is excised, the opening 31 in the sack can be closed by a physician grasping the device 11, holding the finger ring 48 in the palm and using two fingers of the same hand to grasp the finger rings 44 and 46 to pull the same toward the finger ring 48 to close the opening 31 in the sack and to firmly retain the excised body tissue or body part within the sack 21. The device 11 can then be removed from the body cavity and the contents of the sack disposed of thereafter by opening the sack as hereinbefore described and dumping the body tissue or body part therefrom. The device is particularly efficacious in use because of the ease in opening and closing of the sack which is carried by the tubular member.

Another embodiment of the device is shown in FIGS. 6 and 7 in which the distal extremity of the sack 21 extends beyond the distal extremity of tubular member 12. This makes it possible to provide a smaller capsule for the sack because the distal extremity of the sack can be folded over into the capsule and when removed from the capsule can thereafter be deployed in the manner similar to the sack 21 hereinbefore described.

It is apparent from the foregoing that there has been provided a device for collection and removal of body tissue or body parts in laparoscopic surgical procedures which is relatively lightweight and can be made of inexpensive parts so that it can be disposed of after one-time use. The sack is formed in such a manner so that it can be readily opened and closed and when opened will have a large opening to facilitate the gathering of body tissue and/or parts.

What is claimed is:

1. In a device for the collection and removal of body tissue and/or parts in laparoscopic surgery on a patient, an elongate tubular member having proximal and distal extremities and having a bore extending therethrough, a sack formed of a flexible material and having an opening therein, means carried by said tubular member securing at least a side portion of said sack within at least a portion of the length of the distal extremity of said elongate tubular member, drawstring means secured to said sack and circumscribing said opening in said sack for opening and closing said opening in said sack, said drawstring means extending into said bore, slide means slidably mounted on said elongate tubular member and secured to said drawstring means in said bore and handle means secured to the proximal extremity of said tubular member and to said slide means for introducing said sack into the patient and for causing relative movement between the tubular member and the slide means to open said opening in said sack for the collection of body tissue and/or body parts in the patient and to close said opening in said sack after collection of the body tissue and/or parts.

2. A device as in claim 1 together with a capsule having an open end mounted on the distal extremity of the elongate tubular member for enclosing the sack for introduction of the sack into the body cavity of the patient.

3. A device as in claim 2 wherein said sack is movable longitudinally of the capsule to permit the sack to be pushed out from the capsule through the open end and to thereafter permit opening of the sack.

4. A device as in claim 2 together with means carried by the capsule for establishing a sealing engagement between the tubular member and the capsule.

5. A device as in claim 1 wherein said drawstring means for opening and closing of said sack is in the form of a relatively rigid filament which upon movement to open said sack causes the opening of the sack to bow outwardly to facilitate the collection of body tissue and/or parts.

6. A device as in claim 1 wherein the sack has a distal extremity, the distal extremity of said sack extending beyond the distal extremity of the elongate tubular member.

7. A device as in claim 1 wherein said handle means is adapted to be held by the hand of the physician and includes first and second members secured to said slide means adapted to be engaged by fingers of the same hand for causing opening and closing of the opening in said sack.

8. A device as in claim 1 wherein said slide means includes a tubular member co-axially and slidably mounted on the elongate tubular member.

* * * * *